United States Patent [19]
Nakamura et al.

[11] Patent Number: 6,149,818
[45] Date of Patent: Nov. 21, 2000

[54] METHOD FOR SEPARATING COMPONENTS IN LIQUID SPECIMEN AND APPARATUS USED IN SAID METHOD

[75] Inventors: Kenji Nakamura, Amagasaki; Shinji Satomura, Osaka; Masayoshi Hayashi, Kyoto; Hideyoshi Arashima, Kyoto; Tetsushi Okuyama, Kyoto; Nobuhiro Hanafusa, Kyoto; Koji Tanimizu, Kyoto, all of Japan

[73] Assignees: Shimadzu Corporation, Kyoto; Wako Pure Chemical Industries, Ltd., Osaka, both of Japan

[21] Appl. No.: 09/386,149

[22] Filed: Aug. 31, 1999

Related U.S. Application Data

[62] Division of application No. 09/048,327, Mar. 26, 1998.

[30] Foreign Application Priority Data

Apr. 1, 1997 [JP] Japan ..................................... 9-81760

[51] Int. Cl.⁷ .................................................. B01D 15/08
[52] U.S. Cl. ........................................ 210/656; 210/198.2
[58] Field of Search .................................. 210/635, 656, 210/659, 198.2

[56] References Cited

U.S. PATENT DOCUMENTS 5,395,521  3/1995  Jagadeeswaran ..................... 210/198.2
5,618,434  4/1997  Ladisch ................................ 210/198.2
5,693,223  12/1997  Yamada ................................ 210/198.2

*Primary Examiner*—Ernest G. Therkorn
*Attorney, Agent, or Firm*—Armstrong, Westerman, Hattori, McLeland & Naughton

[57] ABSTRACT

The object of the present invention is to provide a method for separating components in a liquid specimen and an apparatus used in said method, by which it is possible to avoid carryover even when the specimen injector is not washed using washing solution and also to avoid the increase of inner pressure in column of the separation device or ineffective separating operation even when many liquid specimens are separated by many times using the same separation device. In the present invention, the liquid specimen is introduced into the separation device from a direction opposite to eluting direction of the separation device which retains an adsorbent, and by separating and eluting the specimen from eluting outlet together with the eluant, trace quantity of insoluble substances and the specimen remained on the specimen introducing passage can be removed by elution procedure. As a result, it is possible to avoid carryover, to prevent the increase of inner pressure in the column of the separation device and to prevent ineffective separating operation caused by clogging of the column.

10 Claims, 12 Drawing Sheets rin A = RINSING BY THE ELUANT A

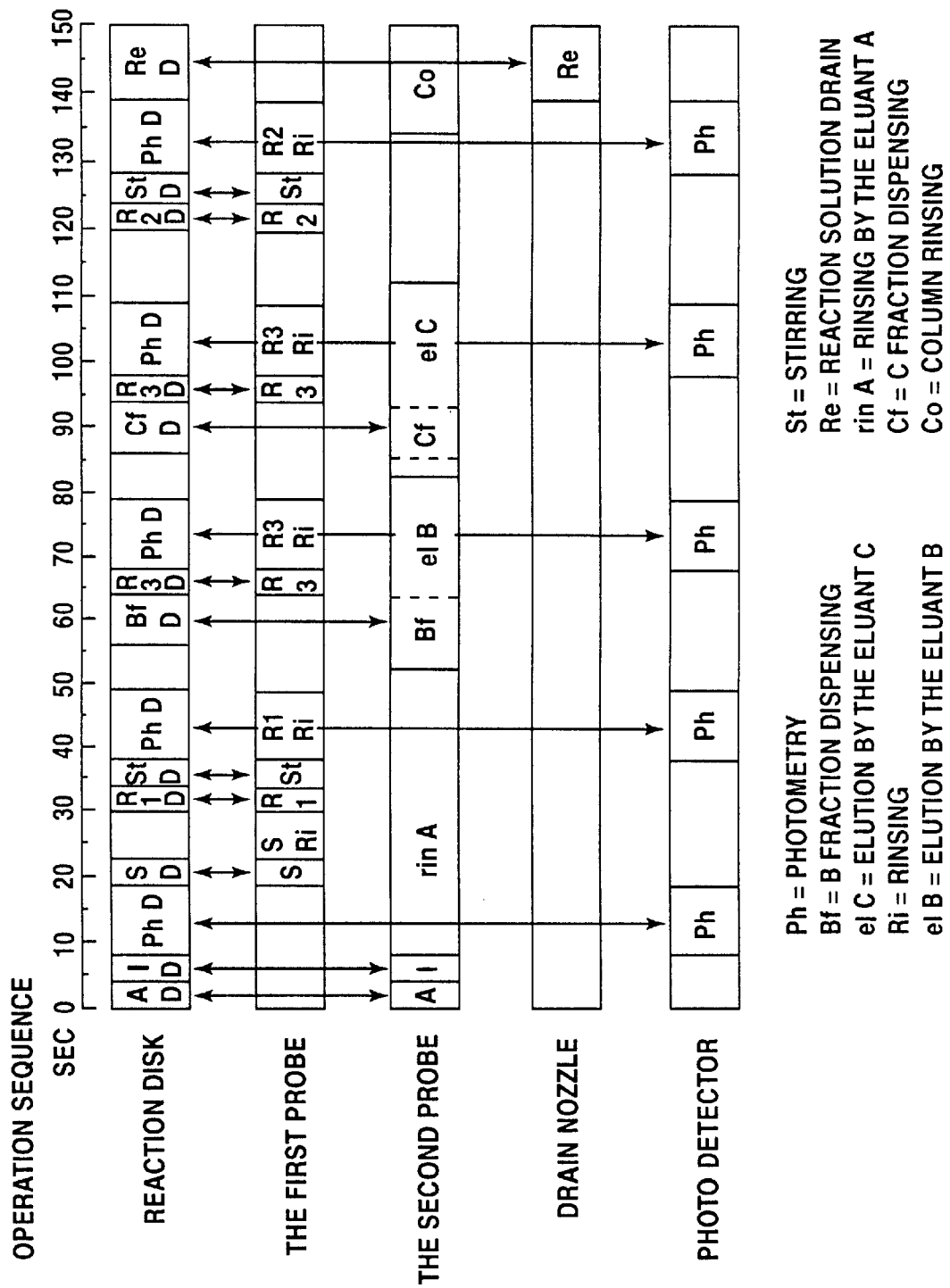

I = INTRODUCE THE REACTION SOLUTION TO THE COLUMN
B = B FRACTION DISPENSING/ R3 DISPENSING
C = C FRACTION DISPENSING/ R3 DISPENSING
rin A = RINSING BY THE ELUANT A

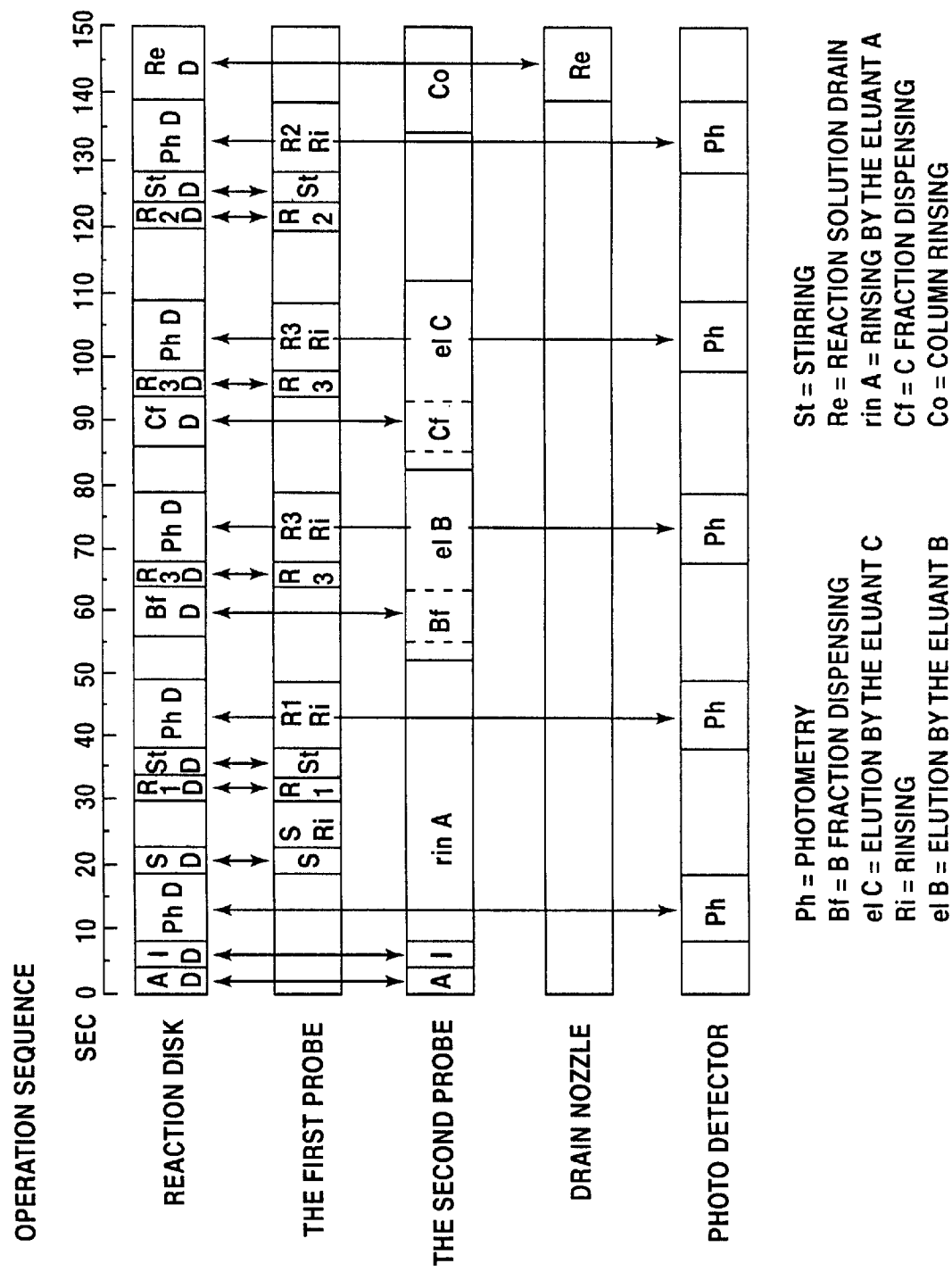

METHOD FOR SEPARATING COMPONENTS IN LIQUID SPECIMEN AND APPARATUS USED IN SAID METHOD

This application is a division of prior application Ser. No. 09/048,327 filed Mar. 26, 1998.

BACKGROUND OF THE INVENTION

The present invention relates to a method for separating two or more components in a liquid specimen by utilizing difference of adsorption to an adsorbent, and also to an apparatus used in said method.

As a method for separating two or more components in a liquid specimen by utilizing difference of adsorption to an adsorbent, a method using column chromatography is generally known.

In general, to introduce a specimen into a column for a column chromatography, the specimen is applied on a column carrier either directly or by means of a specimen injector. The specimen is usually introduced at a site upstream with respect to eluting direction of the specimen.

In the method as described above, as the specimen is introduced from a site upstream of the column, when a column is repeatedly used for separating and/or analyzing many liquid specimens containing insoluble substances not passable through the column such as a serum, the column may be clogged with trace quantity of insoluble substances in the specimen. As a result, pressure in the column may be increased or separation cannot be carried out effectively, and this often leads to problems such as shortening of life of the column. For this reason, pre-treatment such as filtration is generally performed prior to the introduction of the specimen, and components of the specimen are separated after removing insoluble substances. This results in more complicated procedure and reduces working efficiency.

Moreover, in a case where a specimen injector is used, trace quantity of the specimen may remain in the injector and this may cause carryover, which leads to contamination of the specimen to be analyzed. For this reason, after introducing the specimen, it is necessary to wash specimen introducing passage repeatedly using large quantity of washing solution.

SUMMARY OF THE INVENTION

It is an object of the present invention to provide a method for separating components of a liquid specimen and an apparatus used in said method, by which it is possible to avoid the carryover without washing the specimen introducing passage using washing solution.

It is another object of the present invention to provide a method for separating components in a liquid specimen and an apparatus used in said method, by which it is possible to avoid increase of inner pressure of the separating device and to prevent ineffective separating operation even when many liquid specimens are repeatedly separated using the same separation device.

It is still another object of the present invention to provide a method for separating components of a liquid specimen and an apparatus used in said method, which requires no specific type of specimen injector.

To attain the above objects, the method of the present invention for separating two or more components in a liquid specimen by utilizing difference of adsorption to an adsorbent is characterized in that said liquid specimen is introduced into a separation device from a direction opposite to eluting direction of the separation device which retains the adsorbent, and either one of the substance to be measured or impurities dissolved in the liquid specimen, which adversely affect the measurement, is mostly adsorbed on the adsorbent under a condition where the other of the substance or the impurities is eluted, then the adsorbed substances are separated and eluted from the eluting outlet of the device together with the eluant.

Also, the separating apparatus according to the present invention comprises a separation device retaining an adsorbent, a liquid specimen injector arranged separately or integrally at a position closer to the outlet of said separation device, and means for reducing pressure or for reducing and increasing pressure in the separation device connected to the inlet side of said separation device.

According to the present invention, the liquid specimen is introduced into the separation device from a direction opposite to the eluting direction. As a result, trace quantity of insoluble substances is attached to the outlet site of the adsorbent retained in the present device. Thus, the insoluble substances are removed in the initial stage of elution and do not remain in the separation device. This makes it possible to prevent the increase of inner pressure in the separation device caused by clogging of the adsorbent or to avoid ineffective separating operation even when the separating operation is performed repeatedly. Also, it is possible to avoid carryover because the specimen introduced and remaining in the specimen introducing passage, which is leading to the separation device, can be removed by eluting operation.

The above and other objects and advantages of the invention will become more apparent from the description given below.

BRIEF DESCRIPTION OF THE DRAWINGS

FIG. 9(b) shows operation sequence of the apparatus of the present invention in case of one reagent and two eluants;

FIG. 10(b) shows operation sequence of the apparatus of the present invention in case of two reagents and three eluants;

DETAILED DESCRIPTION OF THE PREFERRED EMBODIMENTS

Figure 1:
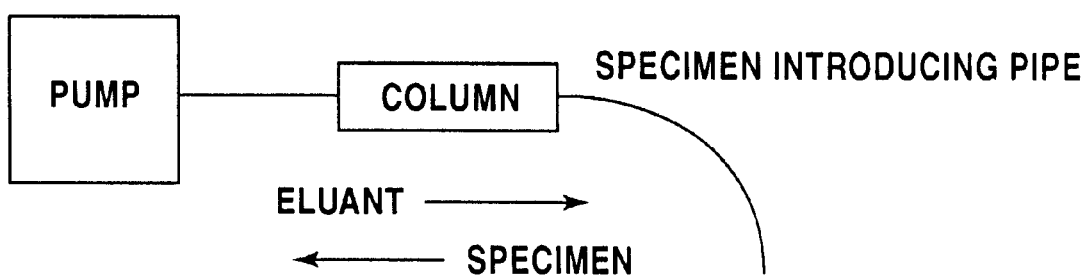
FIG. 1 is a schematical drawing of an apparatus of the present invention.

In the following, description will be given on embodiments of the present invention.

In the method according to the present invention, a liquid specimen is introduced into a separation device from a direction opposite to eluting direction. Accordingly, most of insoluble substances in the liquid specimen are eluted and removed together with the eluant in the initial stage in accordance with the principle of backwash when the eluant is discharge. Also, components adsorbed on the adsorbent are separated by the difference of adsorbing ability.

As the adsorbent used in the present invention, it is preferable to use an adsorbent, which is extremely different in adsorbing ability from a substance A to be measured and impurities B, which adversely affect the measurement. For example, in a case where the above substance A to be measured is to be separated from the impurities B, the following types of adsorbent should be selected: an adsorbent, which adsorbs and elutes the substance A in a quantity more than the measurable quantity under a certain condition but adsorbs and elutes the impurities B only in such a quantity not adversely affecting the measurement, or an adsorbent, which behaves in the same manner as above with respect to the substance A but does not elute the impurities B only in such a quantity not adversely affecting the measurement even when it adsorbs the impurities B in a quantity more than the quantity adversely affecting the measurement, or an adsorbent, which does not adsorb the substance A almost at all but adsorbs most of the impurities B while it does not elute it in a quantity less than the quantity adversely affecting the measurement. Regarding the impurities B', which does not adversely affect the measurement, it does not matter whether it can be separated from the substance A to be measured or not.

It is most effective in the present invention to select an adsorbent, which can almost perfectly adsorb one of either the substance to be measured or the impurities under the condition where the other of the above two substances is eluted. The adsorbent includes the one having properties mentioned below, and when such an adsorbent is used, components adsorbed almost perfectly may be eluted according to the type of adsorption as described below. In this case, the adsorbent may adsorb either the substance to be measured or the impurities, but it is preferable to adsorb the substance to be measured because the impurities usually contain many types of components.

(Ion Exchange)

This type is used for separation of the substances having difference in ionic strength. The substance adsorbed may be eluted by changing ionicity of eluant (i.e. by increasing salt concentration) or by changing pH value.

(Hydrophobic Adsorption)

This relates to separation of the substances, which are hydrophobically different from each other. The substance adsorbed is eluted by decreasing hydrophobic property of the eluant (i.e. by decreasing salt concentration or adding an organic solvent such as methanol, ethanol and acetonitrile).

(Specific Affinity)

This is applied in the separation using substances which show specific adsorbing behavior and used in affinity chromatography, e.g. antigen antibody reaction, substrate and enzyme, receptor and receptor reactive substance (e.g. hormones), lectin and sugar chain, avidin (streptoavidin) and biotin, etc. In this case, the adsorbed substance can be eluted by a known method to dissociate bonding of specific adsorption.

As the adsorbent used in the present invention, it is preferable to use an adsorbent, which can adsorb substances by ion exchange, hydrophobic adsorption or specific affinity as described above, e.g. ion exchange resin, hydrophobic carrier, hydroxyappatite, a protein A fixed affinity carrier, etc.

The thickness of the adsorbent may not be specifically limited and no thick adsorbent may be required, and any conventional film or filter paper having ion exchange ability may be used.

In a case where the liquid specimen is serum, urine, etc., for the purpose of improving the separating efficiency, it is preferable at first to dilute the specimen with a reagent taking a role of solvent and then to introduce the resultant into the separation device. In this case, by adding to the system an antibody to the substance to be measured, an immune complex of "the substance to be measured+the antibody" can be formed, whereby more easy separation by hydrophobic adsorption can be attained because of changing the hydrophobic property of said substance. Further, by introducing an ionic radical into the antibody, an immune complex of "the substance to be measure+the antibody+the ionic radical" can be formed, whereby more easy separation by ion exchange can be attained. Still further, a labeling substance is bonded to an antibody other than the antibody bonded with the ionic radical and then both this labeled antibody and the above ionic radical bonded antibody are combined with the substance to be measured, whereby the ionic radical and the labeling substance can be introduced into the substance to be measured, and use of the thus obtained substance makes it possible to increase specificity to detect the substance to be measured, particularly when a substance not found in a biological component such as human body component is used as the labeling substance. According to the method of the present invention, the substance to be measured in the biological components can be effectively separated from free labeled antibody or substances, which may hinder detection and may be contained in the biological component, and this contributes to the improvement of measurement accuracy.

FIG. 1 is a schematical drawing of an embodiment of a separating apparatus used in the separating method of the present invention. At an eluting outlet of a separation device (column), a specimen introducing pipe is connected, and the other end of the separation device is connected via a pipe to a pump to reduce or increase pressure in the separation device.

As the separation device (separation tube) of the present invention, any type of device may be used so far as it comprises a specimen inlet (elution inlet) and an opening for reducing pressure (for sucking) in the separation device so that the specimen can be introduced therein and that it can retain an adsorbent therein, and its material and shape are not specifically limited. As the separation device, a column in cylindrical shape packed with an adsorbent as normally used in column chromatography may generally be used. For example, an adsorbent prepared in shape of sheet such as filter paper or in shape of membrane is retained in an expanded part (e.g. in disk-like shape) on the tubular portion of the separation device. The specimen inlet is positioned at one end of the separation device, and pressure reducing means is connected to the other end or may be formed on an opening in contact with the atmospheric air. A centrifugal filtration tube packed with an adsorbent in shape of membrane (manufactured by Japan Millipore Ltd.) may also be used.

It is preferable that the separation device is used at vertical position directing the eluting outlet as the lower end. In a case where one of either the substance to be measured or the impurities is adsorbed almost completely, it does not matter whether the eluting outlet is at the upper position in vertical use or on lateral side in horizontal use.

To introduce the liquid specimen from the eluting outlet of the separation device, pressure in the separation device is reduced by a pump as shown in FIG. 1, and the liquid specimen is sucked from the specimen injector into the separation device, i.e. in a direction opposite to the eluting direction.

Even when the eluant is passed through the specimen introducing pipe after the specimen introducing step mentioned above, carryover can be avoided because the eluting outlet and the specimen introducing pipe (specimen introducing passage) are washed with the eluant.

However, to increase measurement sensitivity, it is preferable that, after sucking the liquid specimen, liquid or gas such as air, pure water or eluant is sucked in a quantity higher than the total space volume of the specimen introducing passage so that the liquid specimen attached on the suction passage is flown into the separation device. After introducing the specimen, by introducing gas or liquid in a quantity higher than the total space volume of the specimen introducing passage from the specimen inlet to the adsorbent in the separation device, almost all of the specimen can be introduced into the adsorbent in the separation device, whereby improvement of measurement sensitivity can be attained.

There is no special limitation on the liquid or the gas used for this purpose except the condition that it does not adversely affect separation and measurement.

In a case where the gas in a quantity more than bed volume of the separation device is sucked, it is preferable to select an adsorbent, separation ability of which is not decreased due to suction of the gas.

In a case where the liquid is introduced, it is preferable to optimize sucking speed in order to reduce diffusion of the specimen.

As described above, when the specimen is adsorbed on the adsorbent, eluant is passed from a site upstream of the separation device toward the eluting outlet, i.e. in eluting direction. As the eluant, an eluant normally used in column chromatography may be used according to the type of the adsorbent.

The eluant may be introduced from a site upstream of the separation device (column), i.e. to a pipe between the pump and the separation device in case of the apparatus shown in FIG. 1 or it may be introduced from the specimen introducing pipe. The introduction of the eluant from the specimen introducing pipe can give such merits that the specimen attached on the suction passage can be introduced and the apparatus can be designed in simplified manner.

After the eluant is introduced into the separation device, pressure is increased in the separation device using the pump, and the eluant is eluted together with the specimen components from the eluting outlet directly or through the specimen introducing pipe.

The pump used in the present invention may be any type of pump so far as it can suck the air into or discharge the air from the separation device, and there is no special limitation.

In a case where the pump is used, it is preferable to select such an adsorbent as not giving more than 30 kgf/cm$^2$ load to the pump under the selected condition. By selecting this type of adsorbent, it is possible to introduce smoothly the specimen from the specimen introducing pipe and also to perform smoothly separation and elution under increasing pressure in the separation device.

The means for reducing or increasing pressure may not necessarily be a pump. For example, a rod-like member may be closely and slidably fitted in an outer tube like a syringe so that liquid specimen can be sucked or discharged. In this case, the separation device itself may be used as the outer tube or another pipe different from the separation device may be newly equipped. Or, a cap may be provided, which is expanded to suck and is deflated to discharge just like a pipette.

In the present invention, means for increasing pressure is not necessarily required. The means for reducing or increasing pressure as described above may be removed under sucked condition, and the eluant sucked may be discharged under atmospheric pressure.

The separation of the impurities B and insoluble substances adversely affecting the measurement from the substance A to be measured in the liquid specimen may be conducted as follows:

An adsorbent to adsorb all or most of the substance A (or impurities B) is used, and after sucking the liquid specimen from the eluting outlet, an eluant in such a quantity as not to elute the adsorbed substance A (or impurities B) is sucked from the eluting outlet. By applying pressure, the eluant is passed in the eluting direction to remove most of the insoluble substances and the impurities B (or substance A). Then, the eluant in such a quantity as to elute the adsorbed substance A (or impurities B) is sucked via the eluting outlet. By applying pressure, the eluant is passed in the eluting direction to elute the substance A (or impurities B) adsorbed on the adsorbent, and it is thus recovered.

In a case where the substance A and the insoluble substances are eluted together, the eluant may be divided into two or more fractions in order to separate the substance A, or the eluant may be filtered to separate the substance A.

All of the components adsorbed on the adsorbent as described above are washed away and removed. Thus, it is possible to perform repeatedly the above procedure on another type of liquid specimen using the same separation device.

In the embodiment as described above, the eluant is introduced through the eluting outlet, while it may be introduced from a site upstream of the separation device.

In the above embodiment, the eluant is eluted by applying pressure, while it may be eluted as natural dropping under normal pressure or may be eluted by sucking from the eluting outlet.

In the above embodiment, the specimen introducing pipe is connected to the eluting outlet, while the specimen introducing pipe may not be used if the specimen can be sucked directly, depending upon the shape of the eluting outlet.

In the above embodiment, the liquid specimen is sucked by reducing pressure, and the eluant is then eluted by applying pressure, while it is also possible to introduce the specimen into the separation device from the eluting outlet thereof, which is placed at upper position of the separation device, and then the separation device is turned over to place the eluting outlet at the lower position of the separation device and the eluant is injected from the upper end, whereby the eluant is passed downward under normal pressure. And it is also possible to introduce the specimen from the eluting outlet of the separation device by injecting the specimen to the eluting outlet with the use of an equipment such as a syringe. Among the above, the first mentioned process is preferable, because separation can be carried out quicker.

As the specimen used in the method and the apparatus of the present invention, any liquid specimen used generally in column chromatography may be used. In particular, the method and the apparatus of the present invention are useful for separation of biological components such as serum, which contains trace quantity of insoluble substances.

EXAMPLES

In the following, detailed description will be given on the present invention referring to Examples and Comparative Examples, while the present invention is not limited to these Examples.

Example 1
(1) Preparation of Reagents
(a) Antibody Solution

Figure 2:
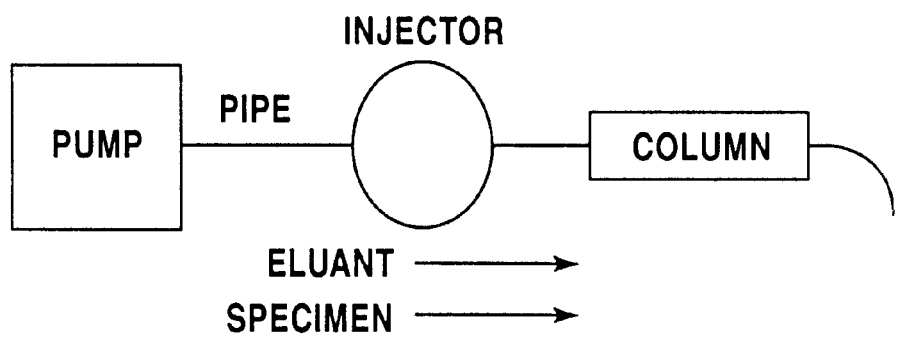
FIG. 2 is a schematical drawing of a conventional type apparatus.
Figure 3:
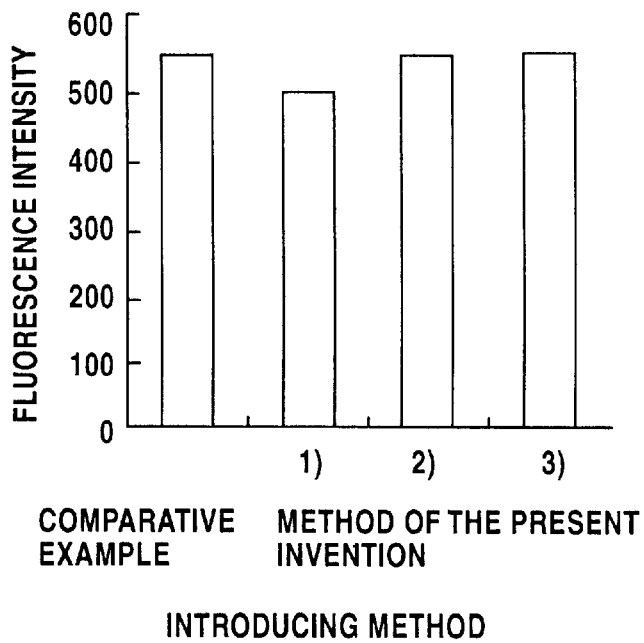
FIG. 3 shows results of measurement of fluorescence intensity of Example 1.

N-(2-acetamide)-2-aminoethane sulfonic acid buffer solution (50 mM; pH 6.5) containing 36.2 $\mu$g/10 ml of peroxydase labeled anti-$\alpha$-fetoprotein antibody Fab'fragment (Fab'-POD; manufactured by Wako Pure Chemical Industries, Ltd.) and 3.7 $\mu$g/10 ml of Fab'fragment produced by conjugating sulfated tyrosine peptide to anti-$\alpha$-fetoprotein antibody, which recognizes the different epitope from that of Fab'-POD (Fab'-YS8; manufactured by Wako Pure Chemical Industries, Ltd.) was prepared, and this was used as antibody solution.
(b) Specimen $\alpha$-fetoprotein (AFP; manufactured by Wako Pure Chemical Industries, Ltd.) was diluted with 50 mM N-(2-acetamide)-2-aminoethane sulfonic acid buffer solution (pH 6.5) to the concentration of 100 ng/ml, and this was used as the specimen.
(c) Substrate Solution Citric acid buffer solution (10 mM; pH 6.5) containing 32 mM 4-acetamide phenol and 38 mM hydrogen peroxide was prepared, and this was used as the substrate solution.
(2) Analytical Procedure The above antibody solution of 100 ml is mixed with 10 $\mu$l of the specimen to allow a reaction to take place at 8° C. for 5 minutes. Then, 80 $\mu$l of the resultant solution was introduced into POROS-DEAE column (0.46×1 cm; manufactured by Perceptive Inc.) by the procedure (a)–(d) given below. Then, the column was washed with 10 ml of 50 mM tris(hydroxymethyl)aminomethane buffer solution (pH 8.0; containing 0.3 M sodium chloride), and an immune complex of Fab'-POD, AFP and Fab'-YS8 was eluted using 3 ml of 50 mM tris(hydroxymethyl)aminomethane buffer solution (pH 8.0; containing 3 M sodium chloride). To 2 ml of the resultant eluate, 200 $\mu$l of the substrate solution was added, and this was reacted at 37° C. for 10 minutes. Then, fluorescence intensity was measured at excitation wavelength of 328 nm and fluorescence wavelength of 432 nm. The results are shown in FIG. 3. The eluant (buffer solution) was introduced from the direction of the pump of the column in all cases.
(3) Specimen Introducing Procedure
(a) Comparative Example An apparatus as shown in FIG. 2 was used, in which a pump (syringe pump; SIL10A; manufactured by Shimadzu Corporation), an injector (Model 7125; manufactured by Rheodyne Inc.), and POROS-DEAE column (separation device) were arranged in this order, and 80 $\mu$l of the specimen was introduced into the column by the injector.
(b) Method (1) of the Present Invention As shown in FIG. 1, POROS-DEAE column was directly connected to the same pump as that of the comparative example, and a specimen introducing pipe with capacity of 100 $\mu$l was connected to the eluting outlet of the column. After sucking 80 $\mu$l of the specimen by pump from the specimen introducing pipe, 100 $\mu$l of the air was sucked.
(c) Method (2) of the Present Invention Using the same apparatus as in (b) above, 80 $\mu$l of the specimen was sucked by pump from the specimen introducing pipe, and 200 $\mu$l of the air was then sucked.
(d) Method (3) of the Present Invention Using the same apparatus as (b) above, 80 $\mu$l of the specimen was sucked by pump from the specimen introducing pipe, and 200 $\mu$l of purified water was then sucked.
(4) Results As it is evident from FIG. 3, fluorescence intensity obtained by the methods (2) and (3) of the present invention is the same as that of the comparative example, while fluorescence intensity obtained by the method (1) of the invention was about 10% lower than that of the comparative example.

This reveals that the measurement sensitivity equal to that of the conventional method can be achieved by thoroughly washing the specimen introducing passage after introducing the specimen.

Although the data are not shown here, fluorescence intensity was measured by the methods (1), (2) and (3) of the present invention on $\alpha$-fetoprotein solutions of different concentrations, and calibration curve showing relationship between concentration of $\alpha$-fetoprotein and fluorescence intensity was prepared on the basis of the measurement. As a result, a calibration curve having satisfactory linearity could be obtained by any of the above methods. This suggests that it is also possible to analyze the desired component with high accuracy by the method (1) of the present invention.

Example 2

Figure 4:
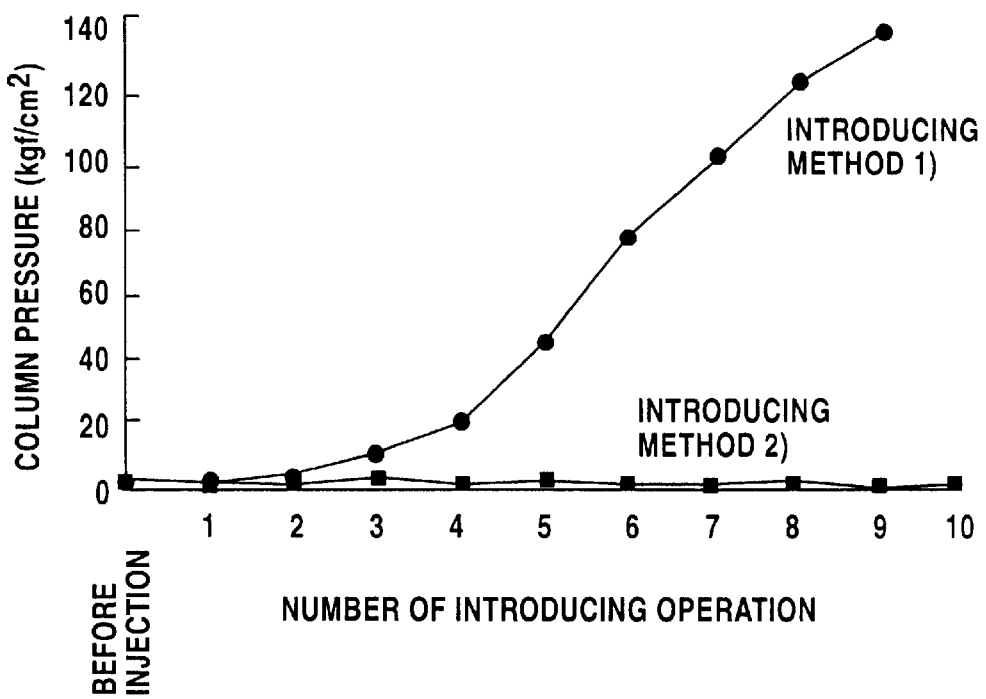
FIG. 4 shows results of measurement of variation in column pressure of Example 2.

Into the same column as the POROS-DEAE column used in Example 1, 100 $\mu$l of human plasma specimen containing insoluble substances was introduced by the procedure described below. Each time the specimen was introduced, 50 mM tris(hydroxymethyl)aminomethane buffer solution (pH 8.0; containing 3 M sodium chloride) was introduced from the pump side to pass through the column at flow rate of 3 ml/min., and the pressure loaded on the column by this procedure was measured. The results are shown in FIG. 4.

Comparative Example
[Introducing Method 1]

As shown in FIG. 2, the apparatus used for comparative example in Example 1 was used, in which a pump, and injector, and a POROS-DEAE column (separation device) were arranged in this order. By the injector, 100 $\mu$l of the specimen was introduced into the column, and 1 ml of the 50 mM tris(hydroxymethyl)aminomethane buffer solution (pH 8.0; containing 3 M sodium chloride) was discharged.
(Method of the Present Invention)
[Introducing Method 2]

As shown in FIG. 1, the same apparatus used for the present invention in Example 1 was used, in which a POROS-DEAE column was directly connected to a pump and a specimen introducing pipe with capacity of 100 $\mu$l was connected to the eluting outlet of the column. From the specimen introducing pipe, 100 μl of the specimen was sucked by the pump, and 200 μl of the purified water was further sucked. Then, by applying pressure using the pump, 1 ml of 50 mM tris(hydroxymethyl)aminomethane buffer solution (pH 8.0; containing 3 M sodium chloride) as an eluant was discharged from a direction opposite to the sucking direction.

As it is clear from FIG. 4, in the introducing method (1) of the comparative example (the conventional method), pressure was increased with the increase of number of introducing operations. On the other hand, in the introducing method (2) of the present invention, no pressure increase was noted almost at all even when the number of introducing operations was increased. These results suggest that it is possible according to the method of the present invention to introduce directly the specimen into the column (separation device) without shortening life of the column, even when the specimen contains insoluble substances.

Example 3

(1) Antibody Solution, Specimen and Substrate Solution
  The same as in Example 1.
(2) Washing Solution and Eluant
  Washing solution: 50 mM tris(hydroxymethyl) aminomethane buffer solution; pH 8.0; containing 0.3 M sodium chloride
  Eluant: 50 mM tris(hydroxymethyl)aminomethane buffer solution; pH 8.0; containing 3 M sodium chloride
(3) Analytical Procedure and Results
  The antibody solution of 100 μl is mixed with 10 μl of the specimen to allow a reaction to take place at 8° C. for 5 minutes.
  To a syringe tube with capacity of 5 ml, Sartobind™ Membrane Adsorber D5F (Abbreviation "MAD5F"; manufactured by Sartorius) was connected. Further, at the eluting outlet of MAD5F, an introducing pipe with capacity of 100 μl was connected.
  By pulling the syringe of the syringe tube, 80 μl of the mixture solution was introduced into the introducing pipe. Then, by pulling the syringe of the syringe tube, 5 ml of the washing solution was introduced from the introducing pipe to the MAD5F. Then, the syringe was pushed to discharge the washing solution to wash MAD5F. This washing procedure was repeated by three times.
  Then, 3 ml of the eluant was sucked and discharged by the same procedure, and an immune complex of Fab'-POD, AFP and Fab'-YS8 was eluted. To 2 ml of the eluate thus obtained, 200 μl of the substrate solution was added, followed by conducting a reaction at 37° C. for 10 minutes. Then, fluorescence intensity was measured at excitation wavelength of 328 nm and fluorescence wavelength of 432 nm. As a result, the fluorescence intensity equal to that of the method (3) of the present invention in Example 1 was obtained.
  These results reveal that the same results can be obtained when the syringe tube is used instead of the pump.

Example 4

Apparatus of the Present Invention

Figure 5:
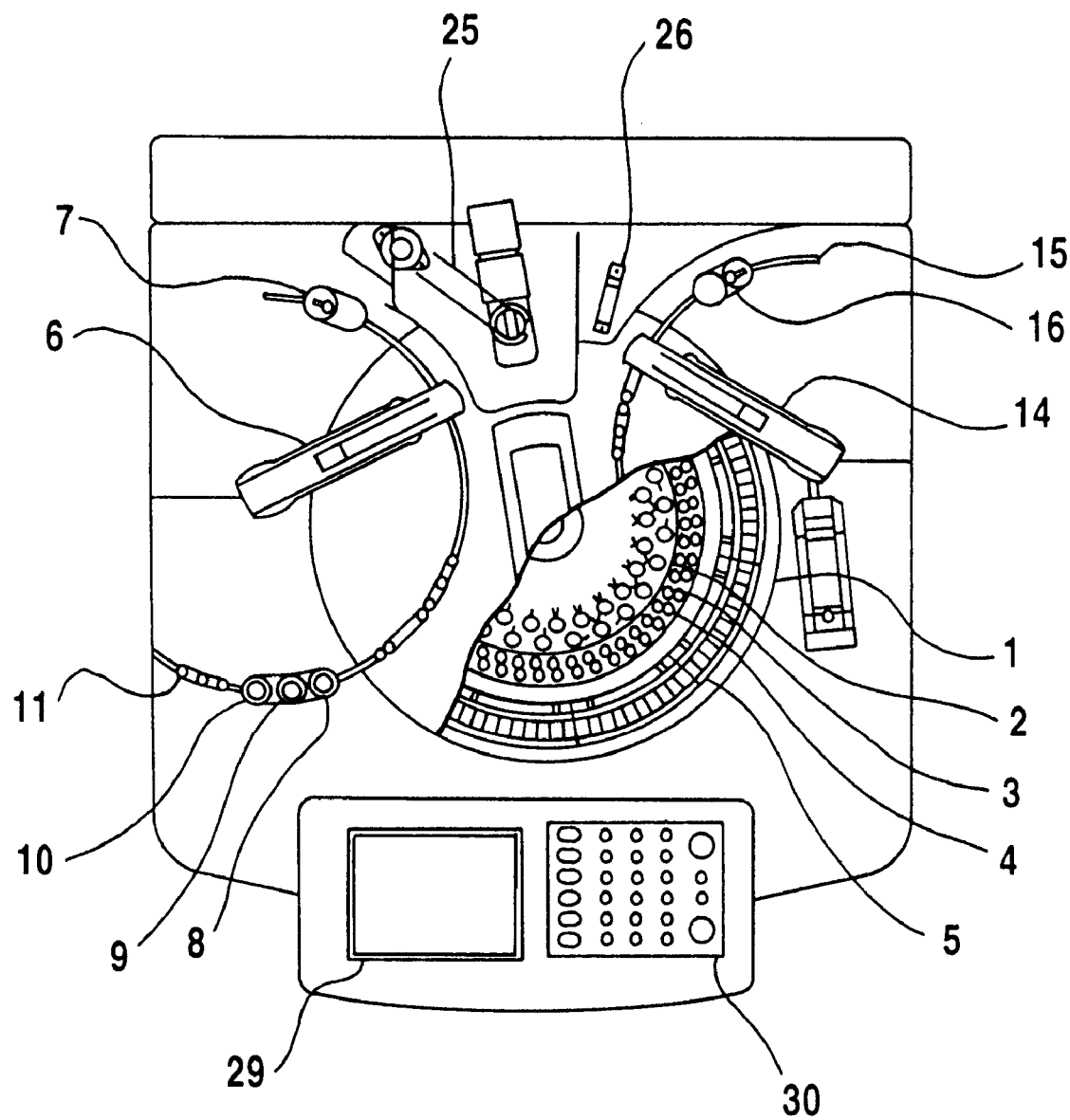
FIG. 5 is a partially cutaway plan view showing an embodiment of the apparatus of the present invention.
Figure 6:
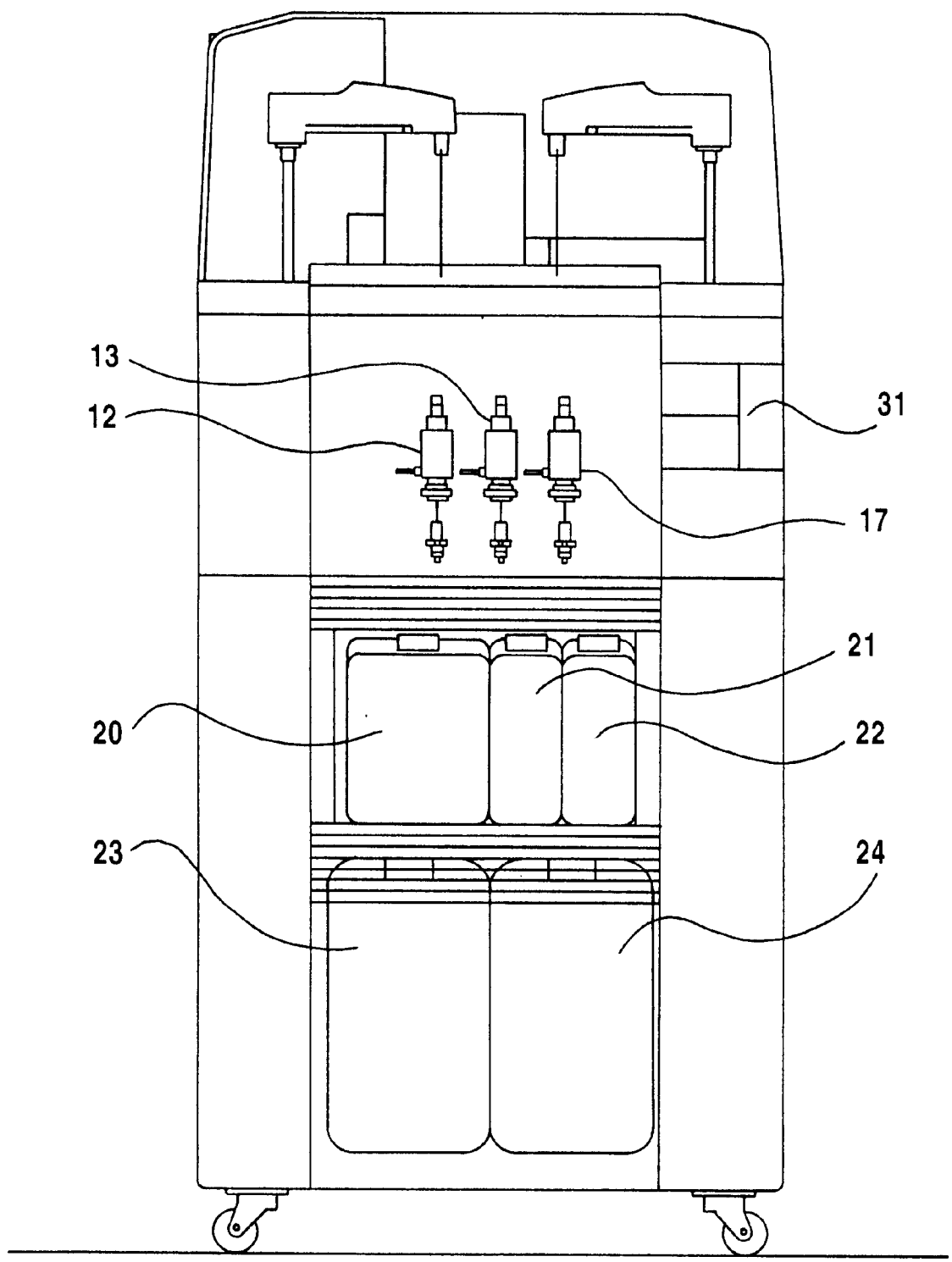
FIG. 6 is a front view of an embodiment of the apparatus of the present invention.
Figure 7:
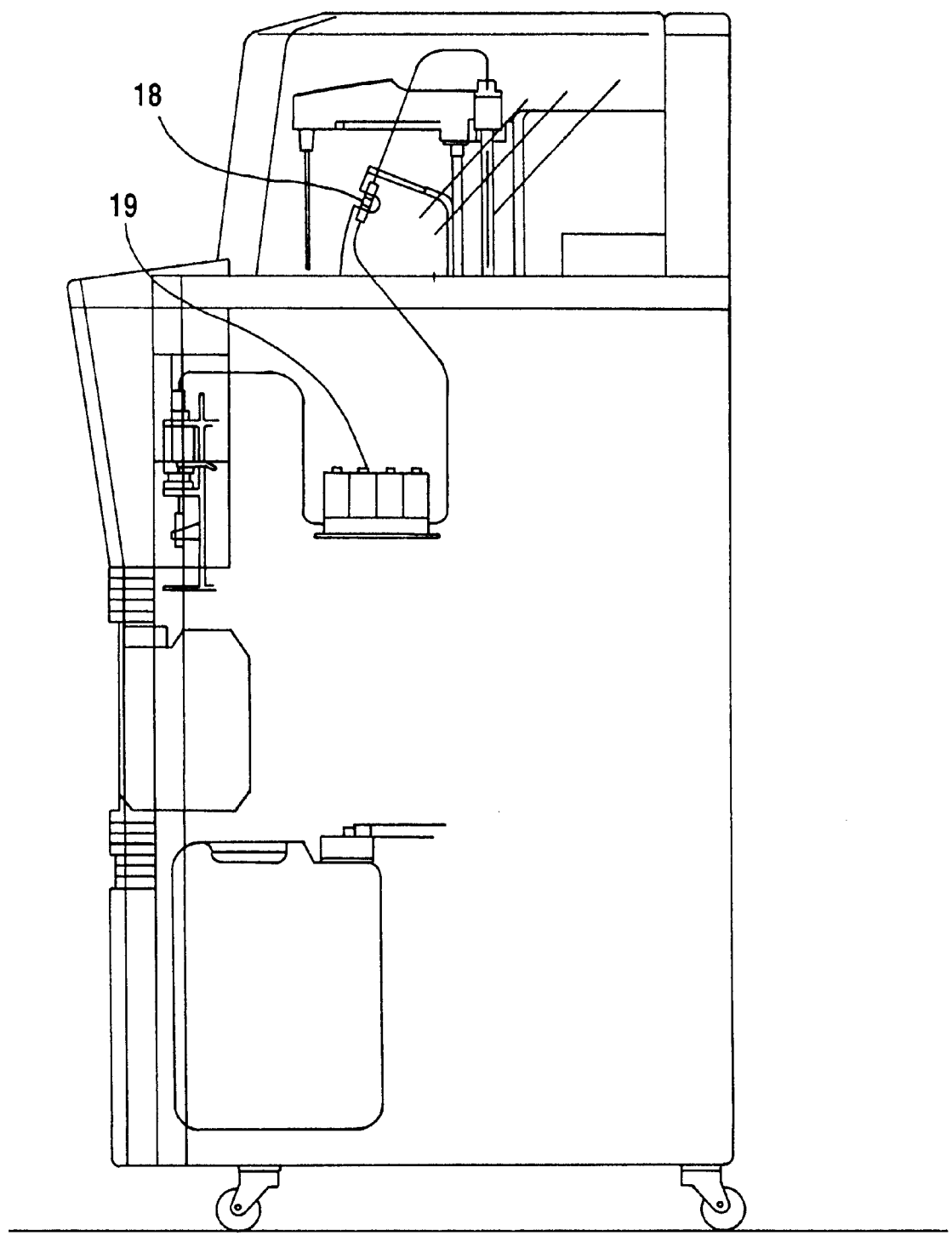
FIG. 7 is a side view of an embodiment of the apparatus of the present invention.
Figure 8:
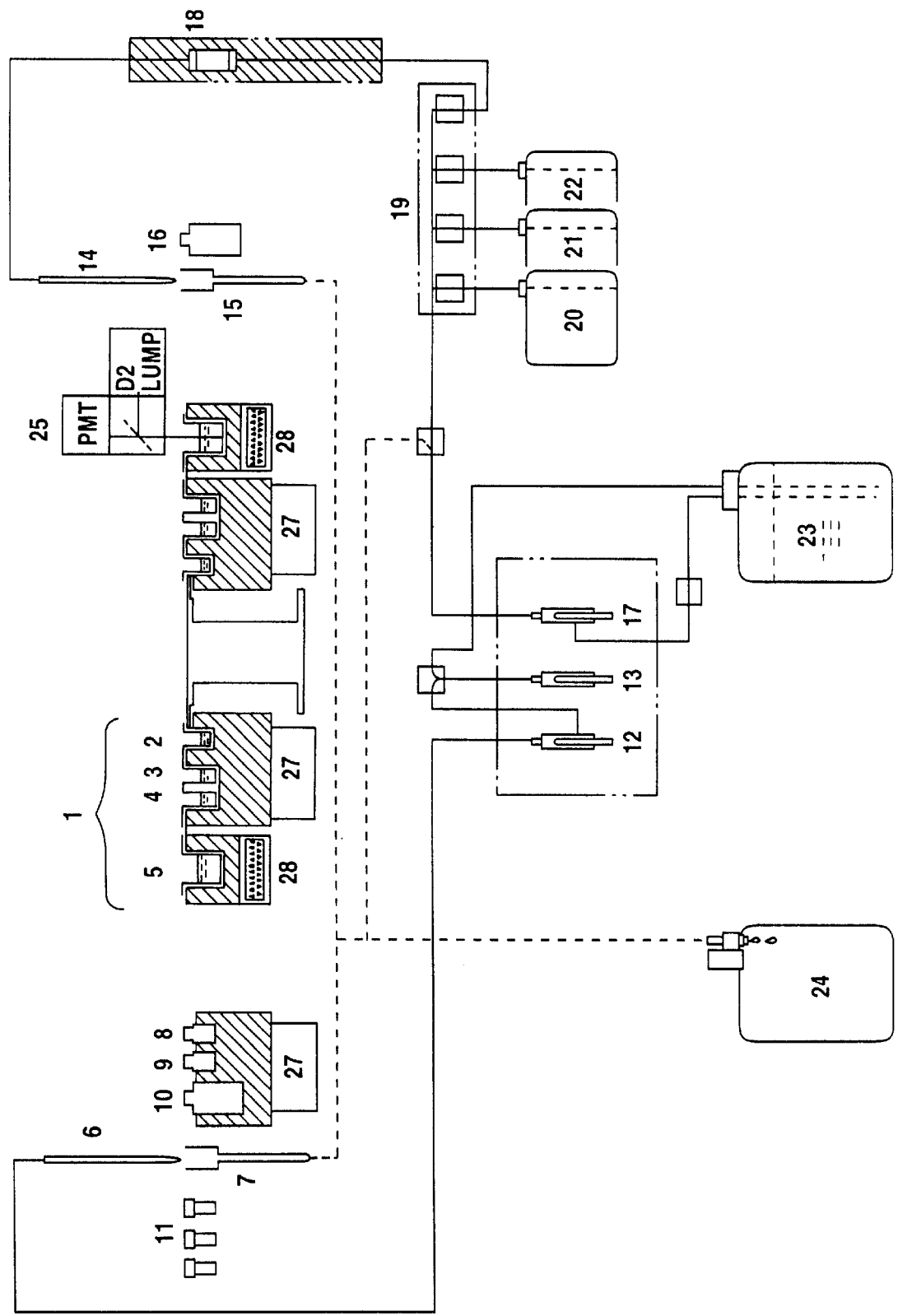
FIG. 8 is a piping system diagram of an embodiment of the apparatus of the present invention.

1. Configuration of the Apparatus
  Description will be given on the system of the apparatus referring to external views of the apparatus of FIG. 5 to FIG. 7 and to the piping system diagram of FIG. 8.
  A reaction disk 1 is a turntable having triple lines, i.e. inner periphery, intermediate periphery and outer periphery. A sample cup 2 is arranged on inner periphery. A cup 3 for antigen-antibody reaction and a cup 4 for the eluant A are arranged on intermediate periphery, and a cell 5 for an enzyme reaction is arranged on outer periphery. The sample cup 2, the cup 3, and the cup 4 are cooled and kept at 8° C. by a cooler unit 27. Temperature of the cell 5 is adjusted to 40° C. by a heating unit 28.

A dispenser unit comprising a first probe 6 sucks the sample contained in the sample cup 2, a first reagent 8, a second reagent 9 (antibody solution), and a third reagent 10 (fluorescence substrate solution) and for dispensing them to the cell 5. The first probe 6 is connected to a pipetting (syringe) pump 12 and a rinsing (syringe) pump 13 via pipe. The probe 6 is sucked, discharged and rinsed using the syringe pumps 12 and 13. Pure water from the pure water tank 23 is filled in the piping. A rinsing pot 7 is used for rinsing the first probe 6. The first probe 6 can also suck a stat sample 11 of a stat sample cup stand.

A dispenser unit comprising a second probe 14 sucks the ummunoreaction solution in the cup 3 and introduces it into the column 18, rinse the column 18 using the eluant A 20 and to dispense the eluant A to the cup 4, and elute the immune complex retained on the adsorbent in the column 18 using the eluant B 21 and/or the eluant C 22 and to dispense the eluant to the cell 5. The second probe 14 is connected to the column (syringe) pump 17 via pipe, and the suction and the drain using the second probe is done by using this syringe pump 17. This pipe is also filled with pure water from the pure water tank 23. A manifold valve 19 is a channel switching valve for switching the eluants A, B and C. A detergent 16 is used to rinse the inside of the column 18 and the inside of the second probe 14. The rinsing pot 15 is used to rinse the second probe 14 and to drain the eluant not used for analysis.

A photo detector 25 is a fluorescence measuring unit to measure fluorescence intensity of the reaction solution in the cell 5. The photo detector 25 irradiates excitation beam to the reaction solution and measures amount of fluorescence emitted from the reaction solution using photomultiplier. The photomultiplier is designed in such manner that it can adjust gain according to the amount of fluorescence.

The drain nozzle 26 is a waste liquid disposal unit to drain the reaction solution after the completion of analysis via a pump (not shown). The waste liquid is accommodated in the drain tank 24.

Pure water to be used for rinsing of probes and piping is accommodated in the pure water tank 23.

Waste liquid of probes and reaction solution are accommodated in the drain tank 24.

A display 29, a keyboard 30, and a printer 31 are control units to request analysis, or to display the results or to give instruction to start the operation.

2. Analysis Procedure Sequence

Analysis procedure sequence indicates flow of operation of each unit in the apparatus of the present invention when a sample is to be analyzed. In other words, it indicates at which timing the sample and the reagent are to be dispensed, reacted, measured by photometry, or drained in a series of analytical operation.
(1) Analysis Procedure Sequence With One Reagent and Two Eluants
  FIG. 9 (*a*) shows analysis procedure sequence in a case where immunoreaction is performed with the first reagent 8 only as pre-treatment and the immune complex is eluted only with the eluant B 21 as the analysis.

1) Preparation

The reagent, the eluants A and B, pure water, the detergent and the column to be used for analysis are set up.

The sample cup 2 is set on inner periphery of the reaction disk 1 and it is cooled down.

The cup 3 for antigen-antibody reaction and the cup 4 for the eluant A are set on intermediate periphery of the reaction disk 1 and is cooled down.

The cell 5 for enzyme reaction is set at outer periphery of the reaction disk 1 and adjusted to 40° C.

The inside of the first probe 6 and the inside of the second probe 14 are rinsed using pure water.

2) After analysis request operation is performed at the system control unit, operation is started.

(a) The reaction disk 1 is operated, and the cup 4 is moved to access position of the second probe 14 [AD]. Next, the second probe 14 dispenses the eluant A to the cup 4 [A].

(b) The reaction disk 1 is operated, and the sample cup 2 is moved to access position of the first probe 6 [SD]. Next, the first probe 6 sucks the sample [S].

(c) The reaction disk 1 is operated, and the cup 3 is moved to access position of the first probe 6 [SD]. Next, the first probe 6 discharges the sample to the cup 3 [S].

(d) The reaction disk 1 is operated, and the cup 3 is moved to access position of the first probe 6 [SD].

(e) The first probe 6 sucks the first reagent (R1) and dispenses it to the cup 3 [R1].

(f) Antigen-antibody reaction is started, and reaction proceeds for about 4.5 minutes.

(g) The reaction disk 1 is operated, and the cup 3 is moved to access position of the second probe 14 [ID]. Next, the second probe 14 sucks the reaction solution [I].

(h) The reaction disk 1 is operated, and the cup 4 is moved to access position of the second probe 14 [AD]. Next, the second probe 14 sucks the eluant A and introduces the reaction solution to the column 18 [I].

(i) The second probe 14 moves to access position of the rinsing pot, and the column 18 is rinsed with the eluant A rinsing by the eluant A.

(j) The second probe moves to access position of the rinsing pot, and the column 18 is rinsed with the eluant B [elution by the eluant B].

(k) The reaction disk 1 is operated, and the cell 5 is moved to access position of the second probe 14 [B fraction dispensing D]. Next, the second probe 14 performs eluting and dispensing of the immune complex to the cell 5 [B fraction dispensing].

(l) The second probe 14 moves to access position of the rinsing pot, and the column 18 is rinsed with the eluant B [elution by the eluant B].

(m) The reaction disk 1 is operated, and the cell 5 is moved to access position of the first probe 6 [R3D]. Next, the first probe 6 sucks the third reagent (R3) and discharge it to the cell 5 [R3].

(n) At this time, an enzyme reaction of the eluent is started.

(o) The reaction disk 1 is operated, and the cell 5 is moved to access position of the photo detector [photometry D]. Next, fluorescence intensity of the reaction solution in the cell 5 is measured [photometry].

(p) Measurement of fluorescence intensity is performed for 10 minutes.

(q) During measurement of fluorescence intensity, the second probe 14 moves to access position of the rinsing pot, and the column 18 and the probe 14 are rinsed [column rinsing].

(r) By a data processing unit (not shown) of the apparatus, data of gain having variation of fluorescence intensity within the measurable range are selected from each photometry data obtained from a plurality of gains, and concentration of the object to be measured in the sample is calculated. At the same time, the result is outputted to the display and the printer.

(s) The reaction disk 1 is operated, and it is moved to access position of the drain nozzle 26 [reaction solution drain D].

(t) At the completion of analytical reaction, the solution is discharged by a pump (not shown).

A series of analytical operation for the sample is now completed.

In this analysis procedure sequence, the second reagent (R2) may be used instead of the first reagent (R1), and the eluant C may be used instead of the eluant B. Also, the first reagent and the second reagent can be switched over to eacgh other, and the eluant B and eluant C can be switched over to each other.

(2) Analysis Procedure Sequence With Two Reagents and Three Eluants

Figure 10A:
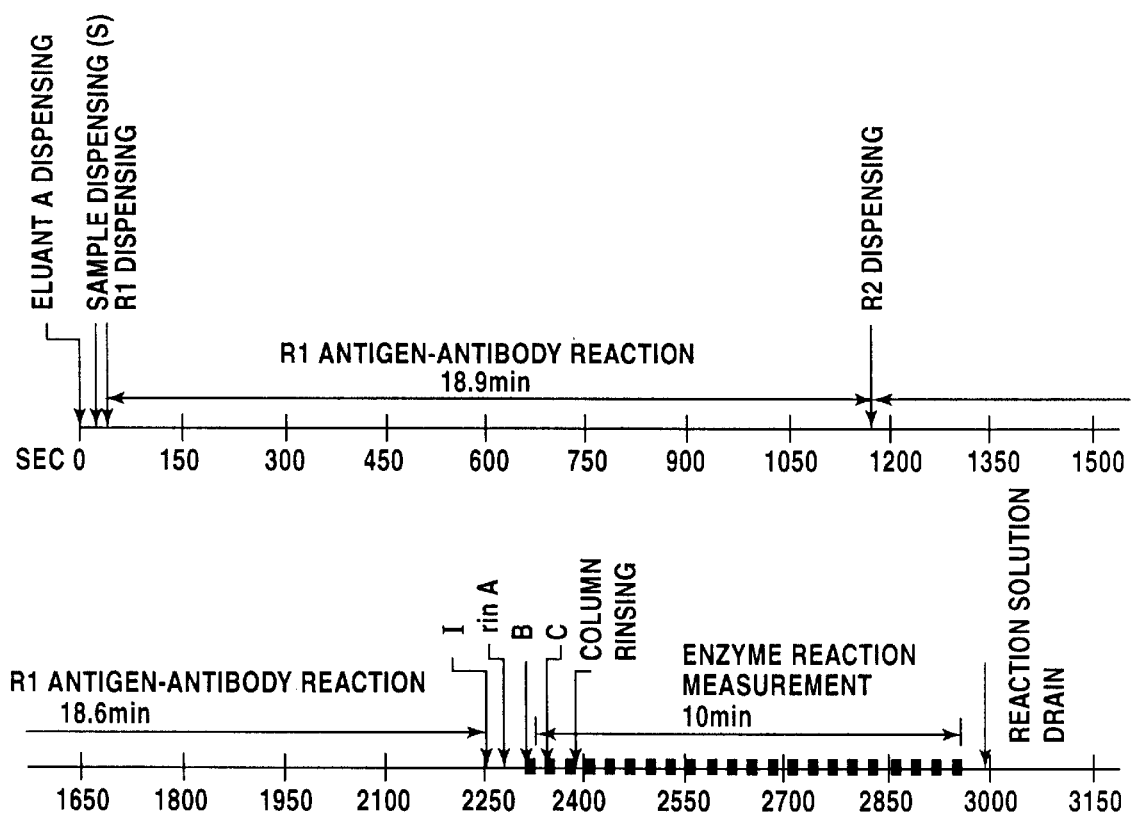
FIG. 10(a) shows analysis procedure sequence using the apparatus of the present invention in case of two reagents and three eluants.

In the above analysis procedure sequence, operation of the first reagent (antibody solution) (R1), the second reagent (R2), and the eluants B and C may be incorporated. FIG. 10 (a) shows an example of the analysis procedure sequence with two reagents and three eluants.

In the present example, the second reagent (R2) is dispensed after 18.9 minutes of dispensing of the first reagent (R1), and the reaction solution is introduced into the column at 18.6 minutes thereafter. After rinsing with the eluant A, elution with the eluant B and elution with the eluant C are carried out one after another, and an enzyme reaction of each eluant is measured by photometry. The results are calculated for each quantity of immune complex eluted with the eluants B and C. Further, using these two data, total quantity of immune complexes and ratio of each immune complex can be calculated.

3. Operation Sequence

Figure 9A:
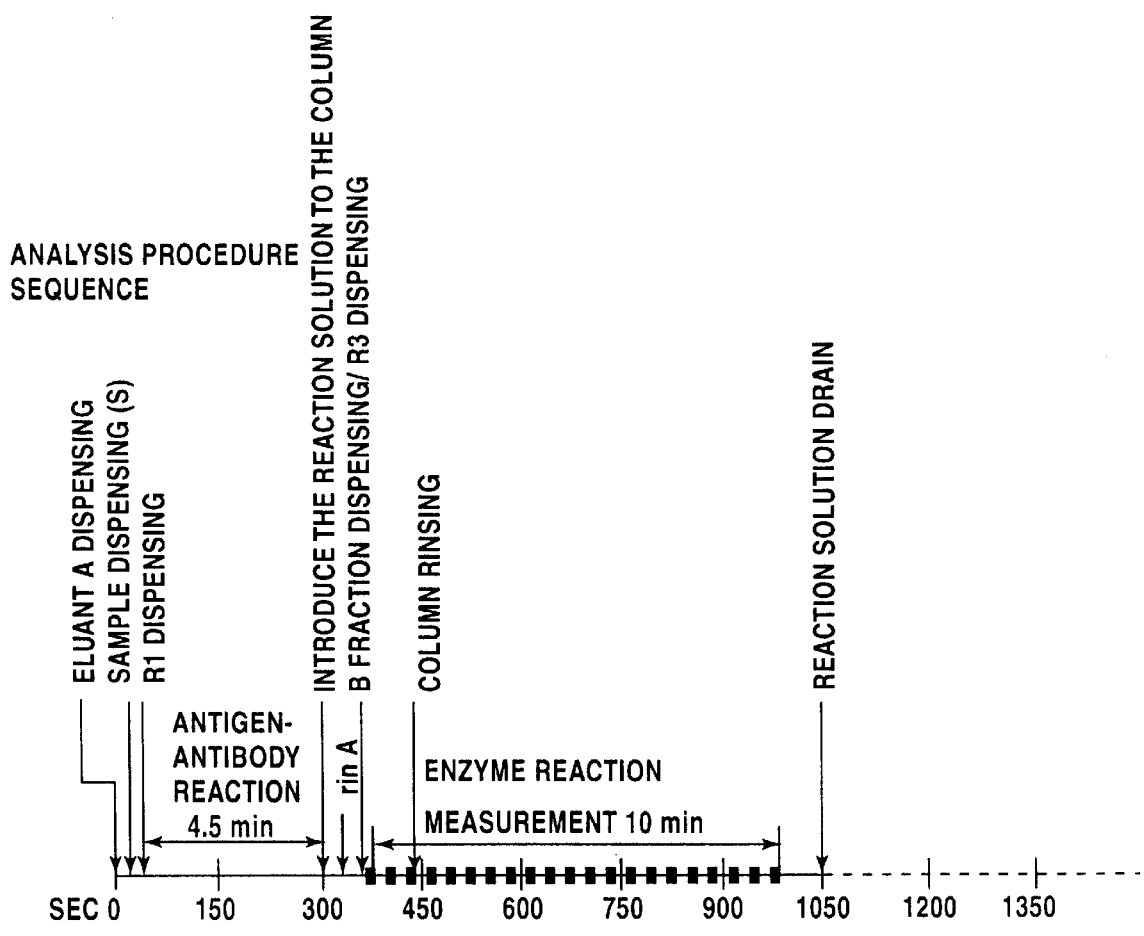
FIG. 9(a) shows analysis procedure sequence of using the apparatus of the present invention in case of one reagent and two eluants.

By repeating the analysis procedure sequence, a plurality of samples can be continuously analyzed. However, when simply repeating the analysis procedure sequence, analysis result only for a single case can be obtained for each duration of a series of analysis procedure sequence. For this reason, in order to increase processing ability, it is generally practiced to operate the apparatus by incorporating operation of the other analysis procedure sequence into an analysis procedure sequence. When operation of the other analysis procedure sequence is incorporated in an analysis procedure sequence, it is called "operation sequence". In the operation sequence of the apparatus, operation of the reaction disk unit is used as basis, and it is based on the duration of the operation of the other unit. In the operation sequence as shown in FIG. 9 (b) and FIG. 10 (b), operation of the other analysis sequence is incorporated at maximum in an analysis sequence, and the time required for carrying out one operation sequence is 150 seconds. By repeating the operation sequence, analysis result is obtained for every 150 seconds in case a plurality of samples are consecutively analyzed. That is, by setting the operation sequence in this manner, processing ability is increased by 7 times in the analysis sequence with one reagent and two eluants and by 20 times in case of analysis sequence with two reagents and three eluants.

4. Operation of Each Unit in Operation Sequence

Detailed description will be given below on operation of each unit.

(1) Operation of Reaction Disk (a) The sign [AD] indicates an operation to move the cup 4 to access position of the second probe 14 in order to dispense the eluant A.

(b) The sign [ID] indicates an operation to move the cup 3 to access position of the second probe 14 in order to suck the antigen-antibody reaction solution.

(c) The sign [photometry] indicates an operation to move the cell 5 to access position of the photo detector 25 in order to perform photometry. This photometry operation is repeated at the same time interval (every 30 seconds in the present example).

(d) the sign [SD] indicates an operation to move the sample cup 2 to access position of the first probe 6 in order to suck the sample, and then to move the cup 3 to access position of the first probe 6 in order to discharge the sample.

(e) The sign [R1D] indicates an operation to move the cup 3 to access position of the first probe 6 in order to dispense the first reagent (R1).

(f) The sign [B fraction dispensing D] and [C fraction dispensing D] each indicates an operation to move the cell 5 to access position of the second probe 14 in order to dispense the eluant of the eluants B or C.

(g) The sign [R3D] indicates an operation to move the cell 5 to access position of the first probe 6 in order to dispense the third reagent (R3).

(h) The sign [R2D] indicates an operation to move the cup 3 to access position of the first probe 6 in order to dispense the second reagent (R2).

(i) The sign [stirring D] indicates an operation to move the cup 3 to access position of the first probe 6 in order to stir up the solution. This operation is not selected in a case where the analysis does not require mixing of the solution.

(j) The sign [reaction solution drain D] indicates an operation to move the cup 3 to access position of the drain nozzle 26 in order to drain the reaction solution after the completion of analysis.

(2) Operation of the First Probe (a) The sign [S] indicates an operation of the first probe 6 to move the access position of the sample cup 2 and to suck the sample, and then to move to access position of the cup 3 and to dispense. Also, the sign [S rinsing] indicates an operation of the first probe 6 to move to access position of the rinsing pot 7 and to perform probe rinsing.

(b) The sign [R1] indicates an operation of the first probe 6 to move to access position of the first reagent (R1) and to suck the reagent (R1), and then to move to access position of the cup 3 and to dispense. The sign [stirring] indicates an operation of the first probe 6 to suck and discharge the reaction solution, and to mix and stir up the solution. This operation is not selected in a case where the analysis does not require mixing of the solution. Further, the sign [R1 rinsing] indicates an operation of the first probe 6 to move to access position of the rinsing pot 7 and to perform probe rinsing.

(c) The sign [R2] indicates an operation of the first probe 6 to move access position of the second reagent (R2) and to such the reagent (R2), and then to move access position of the cup 3 and to dispense. The sign [stirring] indicates an operation of the first probe 6 to suck and discharge the reaction solution, and to mix and stir up the solution. However, this operation is not selected in a case where the analysis does not require mixing of the solution. Further, the sign [R2 rinsing] indicates an operation of the first probe 6 to move to access position of the rinsing pot 7 and to perform probe rinsing.

(d) The sign [R3] indicates an operation of the first probe 6 to move to access position of the third reagent (R3) and to suck the reagent (R3), and then to move to access position of the cell 5 and to dispense. Also, the sign [R3 rinsing] indicates an operation of the first probe 6 to move to access position of the rinsing pot 7 and to perform probe rinsing.

(3) Operation of the Second Probe (a) The sign [A] indicates an operation of the second probe 14 to move to access position of the rinsing pot 15, to replace the content in the piping with the eluant A by sucking and discharging the eluant A using the column syringe pump, and then to move to access position of the cup 4 and to dispense the eluant A.

(b) The sign [I] indicates an operation of the second probe 14 to move to access position of the cup 3 and to suck the antigen-antibody reaction solution, and then to move to access position of the cup 4, and to introduce the antigen-antibody reaction solution into the column 18 by sucking the eluant A.

(c) The sign [rinsing by the eluant A] indicates an operation of the second probe 14 to move access position of the rinsing pot 15, and to perform column rinsing with the eluant A by repeating suction and discharge of the eluant A using the column syringe pump.

(d) The sign [elution by the eluant B] indicates an operation of the second probe 14 to move to access position of the rinsing pot 15 and to elute the column-adsorbed immune complex with the eluant B by repeating suction and discharge of the eluant B using column syringe pump. Also, the sign [B fraction dispensing] indicates an operation of the second probe 14 to move to access position of the cell 5 and to discharge the eluant.

(e) The sign [elution by the eluant C] indicates an operation of the second probe 14 to move to access position of the rinsing pot 15 and to elute the column-adsorbed immune complex with the eluant C by repeating suction and discharge of the eluant C using the column syringe pump. Also, the sign [C fraction dispensing] indicates an operation of the second probe 14 to move to access position of the cell 5 and to discharge the eluant.

(f) The sign [column rinsing] indicates an operation of the second probe 14 to move to access position of the rinsing pot 15 and to move to access position of the detergent after rinsing the column and the probe by repeating suction and discharge of pure water using the column syringe pump. It also indicates an operation that the detergents is introduced into the column and is moved to access position of the rinsing pot 15, and rinsing with detergent is performed by repeating suction and discharge of pure water again using the column syringe pump.

(4) Operation of Drain Nozzle (a) The sign [reaction solution drain] indicates an operation that the drain nozzle 26 is placed into the cup 3 which has been mooved to access position of the drain nozzle 26 and the reaction solution is drained after the completion of analysis.

(5) Operation of Photo Detector (a) The sign [photometry] indicates an operation that fluorescence is measured on the reaction solution in the cell 5, which has been moved to access position of the photo detector. In this [photometry], consecutive photometry of 5 cells during reaction is defined as one operation, and 5 operations (every 30 seconds in the present example) are repeated during one cycle at the same interval.

5. Note

It is needless to say that the term such as operation time of each unit, reaction time, number of sample cups and various types of cup(s) 3 as well as suction and discharge amount of each solution, preset temperature, analysis procedure sequence and operation sequence, etc. are not limited to those described above, and that these can be changed or modified.

Example 5

Measurement of AFP (1) The Apparatus

The apparatus of Example 4 was used.

(2) Preparation of the Reagents (a) Antibody solution

The same antibody solution as in Example 1 was used, and this was set to the position of the reagent 1 (R1) in the apparatus of Example 4.

(b) Sample

Human serum with AFP concentration of 420 ng/ml was diluted with physiological saline to 1/10, 2/10, 3/10, 4/10, 5/10, 6/10, 7/10, 8/10 and 9/10 respectively, and these were used as samples. Also, a standard solution having AFP concentration of 100 ng/ml (manufactured by Wako Pure Chemical Industries, Ltd.) was used as a standard solution.

(c) Substrate solution

The same substrate solution as in Example 1 was used, and this was set to the position of the reagent 3 (R3) in the apparatus of Example 4.

(d) Eluants

Eluant A: 50 mM tris(hydroxymethyl)aminomethane buffer solution (pH 8.0; containing 0.3 M sodium chloride)

Eluant B: 50 mM tris(hydroxymethyl)aminomethane buffer solution (pH 8.0; containing 8.0 M sodium chloride)

These two eluants were set to the positions of the eluants A and B respectively in the apparatus of Example 4.

(3) Analytical Procedure

Using the analysis procedure sequence 1 (one reagent, two eluants) of Example 4, analysis was performed under the following analytical conditions, and the change of fluorescence intensity per minute was determined for each sample. The measured values were compared with the measured value of AFP standard solution, and AFP concentration in each sample was calculated. For each sample, five measurements were performed.

The first reagent: 100 μl

Sample: 3 μl

Quantity of antigen-antibody reaction solution applied into column: 20 μl

Quantity of substrate solution: 100 μl

Quantity of fraction: 1 ml

Quantity of column rinsing solution: 18 ml

Column: POROSE-DEAE column (5.5×6.9 mm; manufactured by Perceptive Inc.)

RESULTS

Figure 11:
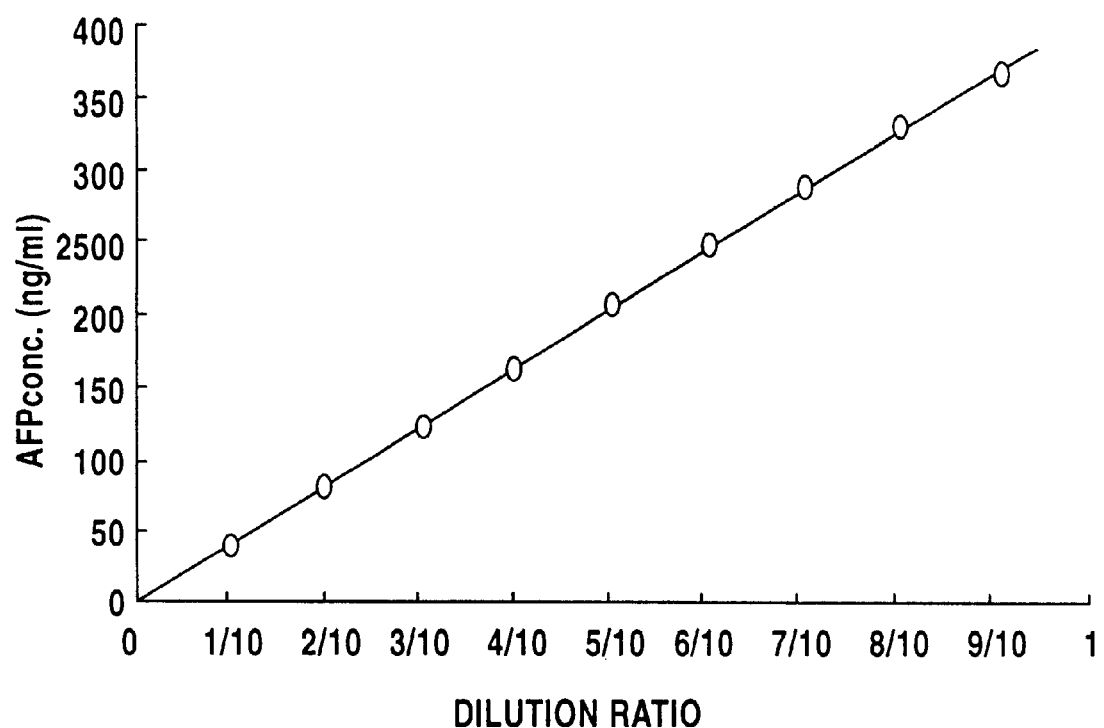
FIG. 11 is a calibration curve showing the relation between dilution ratio and α-fetoprotein (AFP) concentration value according to Example 5.

FIG. 11 shows relation between dilution ratio and measured values. As it is clear from FIG. 11, there is a good linear relation passing through the origin. When coefficient of variation was obtained for each sample, the values were satisfactory, being 0.8% to 6.0%.

Example 6

Differential Measurement of AFP Having Different Sugar Chain Structures (1) The Apparatus The apparatus of Example 4 was used.

(2) Preparation of the Reagents.

(a) The first reagent

First, 50 mM N-(2-acetamide)-2-aminoethane sulfonic acid (ACES) buffer solution (pH 6.5) was prepared, which contains 10 mg/10 ml of lentil lectin (LCA; manufactured by Honen Corporation) and 1.75 nmol/10 ml of anti-α-fetoprotein antibody Fab' fragment conjugated with sulfated tyrosine-peptide having 5 sulfuric acid residue groups [Ala-(Tyr($SO_3$)$_5$)]. (Fab'-YS5; manufactured by Wako Pure Chemical Industries, Ltd.) This was used as the first reagent and was set to the position of the reagent 1 in the apparatus of Example 4.

(b) The second reagent

First, 50 mM ACES buffer solution (pH 6.5) was prepared, which contains 402 pmol/ml of peroxidase-labeled anti-α-fetoprotein antibody Fab' fragment proven to recognize the different epitope from that of Fab'-YS5 as described above (Fab'-POD; manufactured by Wako Pure Chemical Industries, Ltd.) and 72 pmol/ml of Fab' fragment of anti-α-fetoprotein antibody proven to recognize the different epitope from that of Fab'-YS5 and Fab'-POD conjugated with sulfated tyrosine-peptide having 8 sulfuric acid residue groups [Ala-(Tyr($SO_3$)$_5$)] (Fab'-YS8; manufactured by Wako Pure Chemical Industries, Ltd.). This was used as the second reagent and was set to the position of the reagent 2 (R2) in the apparatus of Example 4.

The antibody used for preparation of Fab'-YS8 has property to be bound only with AFP not bound with LCA. In contrast, the antibody used to prepare Fab'-YS5 and Fab'-POD has property to be bound to all types of AFP regardless of whether the binding with LCA is present or not.

(c) Samples

Human serum having AFP concentration of 690 ng/ml and AFP-L3 fraction ratio (%) of 46% was diluted with physiological saline to 1/10, 2/10, 3/10, 4/10, 5/10, 6/10, 7/10, 8/10 and 9/10 respectively, and these were used as samples. Also, a standard solution having AFP concentration of 200 ng/ml and AFP-L3 fraction ratio (%) of 0% and a standard solution having AFP concentration of 200 ng/ml and AFP-L3 fraction ratio (%) of 100% (both manufactured by Wako Pure Chemical Industries, Ltd.) were used as standard solutions, and a calibration curve was prepared.

(d) Substrate solution

The same substrate solution as in Example 1 was used, and this was set to the position of the reagent 3 (R3) in the apparatus of Example 4.

(e) Eluants

Eluant A: 50 mM tris(hydroxymethyl)aminomethane buffer solution (pH 8.0; containing 0.3 M sodium chloride)

Eluant B: 50 mM tris(hydroxymethyl)aminomethane buffer solution (pH 8.0; containing 0.78 M sodium chloride)

Eluant C: 50 mM tris(hydroxymethyl)aminomethane buffer solution (pH 8.0; containing 3.0 M sodium chloride)

These three buffer solutions were used as eluants, and these were set to the positions of eluants A, B and C respectively in the apparatus of Example 4.

(3) Analytical Procedure

Using the analysis procedure sequence 2 of Example 4 (two reagents, three eluants), analysis was performed under the conditions given below.

The immune complex 1 (Fab'-POD-AFP-Fab'-YS5) was eluted with the eluant B from the column and the immune complex 2 (Fab'-POD-AFP-Fab'-YS8-Fab'-YS5) was eluted with the eluant C from the column. For each of the fractions of the immune complex 1 and the immune complex 2, the change of fluorescence intensity per minute was measured. From the sum of the measured values thus obtained and the measured values of AFP standard solutions, AFP concentration in each sample was calculated.

The measured values of the fraction of the immune complex 1 and the immune complex 2 were introduced to the equation given below, and the fraction ratio (%) of each sample was calculated. The result was applied to the calibration curve, which had been prepared using the fraction ratio obtained by same procedure from the standard solution having L3 fraction ratio of 0% and AFP standard solution having L3 fraction ratio of 100%, and AFP-L3 fraction ratio (%) in each sample was calculated.

Fraction ratio (%)=Measured value of fraction of immune complex 1/(Measured value of fraction of immune complex 1+Measured value of fraction of immune complex 2)

The first reagent: 100 μl
The second reagent: 10 μl
Sample: 10 μl
Quantity of antigen-antibody reaction solution applied into column: 80 μl
Quantity of substrate solution: 100 μl
Quantity of fraction of immune complex 1: 1 ml
Quantity of fraction of immune complex 2: 1 ml
Quantity of column rinsing solution: 18 ml
Column: POROSE-DEAE column (5.5×6.9 mm)

RESULTS

Figure 12:
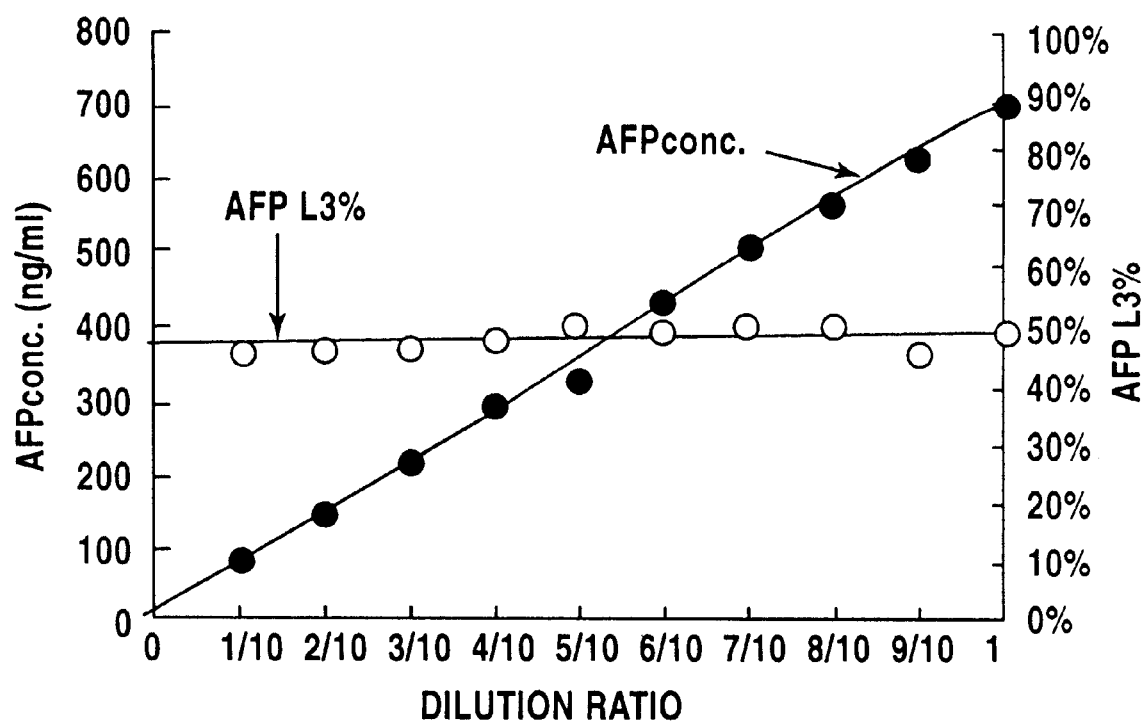
FIG. 12 is calibration curves showing the relation between dilution ratio and α-fetoprotein (AFP) concentration and the relation between dilution ratio and AFP-L$_3$ fraction ratio according to Example 6.

FIG. 12 shows relation between dilution ratio and the measured values. As it is clear from FIG. 12, AFP concentration shows good linear relation passing through the origin. Also, it is clear that AFP-L3 fraction ratio (%) does not change even when the sample is diluted. This is because the ratio of AFP to react with a specific type of lectin (having specific sugar chain structure) does not vary even when the sample is diluted.

According to the present invention, it is possible to avoid pressure increase in the separation pipe or ineffective separation even when separation procedure is performed many times. Accordingly, the problems not solvable by the conventional technique can be overcome, i.e. it is possible to avoid carryover, and life of the separation device can be extremely improved. Therefore, the present invention has novelty and it is an epoch-making invention.

In case pressurized elution is performed using pump, the specimen is introduced from open end of the eluting outlet in the present invention, and there is no need to use specific type of specimen injector.

What is claimed is:

1. A method for separating two or more components in a liquid specimen, utilizing difference of adsorption to an adsorbent, comprising the steps of introducing the liquid specimen from a direction opposite to eluting direction of a separation device which retains the adsorbent and has an eluant inlet connected to an eluant supply, and of separating and eluting the components from the eluting outlet together with an eluant, whereby specimen carry over is avoided.

2. A separating method according to claim 1, wherein said liquid specimen is introduced into said separation device by sucking or injecting.

3. A separating method according to claim 2, wherein said eluant is introduced into the separation device by sucking from a direction opposite to eluting direction of said separation device.

4. A separating method according to claim 2, wherein, after sucking said liquid specimen, gas or liquid is sucked, and the liquid specimen remained on a suction passage is passed into said separation device.

5. A separating method according to claim 4, wherein pressure is increased in eluting direction in said separation device to separate and elute the adsorbed liquid specimen.

6. A separating method according to claim 5, wherein adsorption and elution of said liquid specimen on the adsorbent are repeatedly performed on other type of liquid specimen using the same separation pipe.

7. A separating method according to claim 1, wherein said liquid specimen is a specimen containing insoluble substances.

8. A separating method according to claim 7, wherein either one of the substance to be measured or impurities adversely affecting the measurement as dissolved in said liquid specimen is mostly adsorbed on said adsorbent under a condition where the other of said substance or impurities is eluted.

9. A separating method according to claim 1, wherein the separation device retaining said adsorbent is a column filled with the adsorbent.

10. A separating method according to claim 1, wherein the separation device retaining said adsorbent retains the adsorbent in shape of sheet or membrane in a tubular portion of said device or in an expanded part formed on the tubular portion.

* * * * *